United States Patent
Pizzini (10) Patent No.: US 9,526,809 B2
(45) Date of Patent: Dec. 27, 2016

(54) AROMATHERAPY DEVICE

(71) Applicant: Institute for Cancer Research, Philadelphia, PA (US)

(72) Inventor: Mark-Alan Pizzini, Wynnewood, PA (US)

(73) Assignee: Institute for Cancer Research, Philadelphia, PA (US)

( * ) Notice: Subject to any disclaimer, the term of this patent is extended or adjusted under 35 U.S.C. 154(b) by 171 days.

(21) Appl. No.: 14/207,789

(22) Filed: Mar. 13, 2014

(65) Prior Publication Data

US 2014/0193764 A1    Jul. 10, 2014

Related U.S. Application Data

(63) Continuation of application No. PCT/US2012/055888, filed on Sep. 18, 2012.

(60) Provisional application No. 61/536,228, filed on Sep. 19, 2011.

(51) Int. Cl.
| | |
|---|---|
| A61L 9/12 | (2006.01) |
| A61M 11/04 | (2006.01) |
| A61M 15/08 | (2006.01) |
| A61M 21/00 | (2006.01) |
| A61M 15/00 | (2006.01) |
| A61L 9/03 | (2006.01) |
| A61M 21/02 | (2006.01) |

(52) U.S. Cl.
CPC .. *A61L 9/12* (2013.01); *A61L 9/03* (2013.01); *A61L 9/127* (2013.01); *A61M 11/041* (2013.01); *A61M 11/042* (2014.02); *A61M 15/003* (2014.02); *A61M 15/0003* (2014.02); *A61M 15/0035* (2014.02); *A61M 15/0041* (2014.02); *A61M 15/08* (2013.01); *A61M 15/085* (2014.02); *A61M 21/00* (2013.01); *A41D 2400/36* (2013.01); *A61L 2209/133* (2013.01); *A61M 21/02* (2013.01); *A61M 2021/0016* (2013.01); *A61M 2209/088* (2013.01)

(58) Field of Classification Search
CPC ....... A61L 9/12; A61L 9/127; A61L 2209/133
See application file for complete search history.

(56) References Cited

U.S. PATENT DOCUMENTS

| | | | |
|---|---|---|---|
| 3,286,872 A | 11/1966 | Burdick, Jr. | |
| 4,161,284 A * | 7/1979 | Rattan ....................... | A61L 9/12 239/43 |
| 4,247,042 A * | 1/1981 | Schimanski ........ | A01M 1/2044 239/43 |
| 4,402,433 A | 9/1983 | Webinger | |
| 4,526,320 A * | 7/1985 | von Philipp ........ | A01M 1/2044 239/34 |

(Continued)

OTHER PUBLICATIONS

International Search Report dated Nov. 30, 2012, issued in parent application, PCT/US2012/055888.

*Primary Examiner* — Ryan Reis
(74) *Attorney, Agent, or Firm* — Stradley Ronon Stevens & Young, LLP (57) ABSTRACT

The invention provides aromatherapy devices that may be used to break a capsule containing a desired aromatic liquid, and then control the release of the aroma as the volatile aromatic liquid evaporates. The devices may be used, for example, in aromatherapy, including to control nausea or to mask unpleasant scents.

21 Claims, 8 Drawing Sheets

(56) References Cited

U.S. PATENT DOCUMENTS

| | | | |
|---|---|---|---|
| 4,630,775 A * | 12/1986 | Mandon | A01M 1/2044 |
| | | | 239/56 |
| 5,318,503 A | 6/1994 | Lord | |
| 6,834,847 B2 | 12/2004 | Bartsch et al. | |
| 7,004,167 B2 | 2/2006 | Cheng | |
| 7,344,740 B2 | 3/2008 | Vail, III et al. | |
| 7,614,568 B2 * | 11/2009 | Joshi | A61L 9/037 |
| | | | 222/386.5 |
| 2006/0157578 A1 | 7/2006 | Harada et al. | |
| 2008/0060116 A1 | 3/2008 | Massage | |
| 2012/0061487 A1 * | 3/2012 | Fortin | A61L 9/03 |
| | | | 239/36 |

* cited by examiner

AROMATHERAPY DEVICE

CROSS REFERENCE TO RELATED APPLICATIONS

This application is a continuation of International Application No. PCT/US2012/055888 filed Sep. 18, 2012, which claims priority to U.S. Provisional Application No. 61/536,228 filed on Sep. 19, 2011, the contents of each application are incorporated by reference herein, in their entirety and for all purposes.

FIELD OF THE INVENTION

The invention relates to the field of medical devices, such as diffusers of aromatics. More particularly, the invention relates to devices that may be placed in articles of clothing or apparel in order to release desired scents to induce physiological and psychological effects in the wearer.

BACKGROUND OF THE INVENTION

Various publications, including patents, published applications, technical articles and scholarly articles are cited throughout the specification. Each of these cited publications is incorporated by reference, in its entirety and for all purposes, in this document.

The olfactory senses have powerful physiological and psychological effects. Different scents elicit different responses from individuals. These responses may include anti-emetic properties, bronchodilation, calming effects, and other positive emotions. For example, aromatherapy may be used to help patients with postoperative nausea and vomiting and to relieve tension and stress.

Diffusers of aromatics for aromatherapy are known. These diffusers include candles, room fresheners, cartridges, patches, bandannas, gloves, and wristbands. For example, U.S. Publication No. 2008/0060116 discloses a plastic wristband with an aroma impregnated therein. Although this wristband provides aromatherapy, the aroma will disappear after wear and the wristband will no longer be useful for aromatherapy.

U.S. Publication No. 2006/0157578 also discloses a diffuser with a flexible casing and a liquid-impermeable/breakable capsule enclosing a volatile aromatic liquid. When the casing is bent, the capsule breaks and the volatile liquid is temporarily held by a liquid-absorbent member and gradually volatizes and diffuses through a vent hole.

SUMMARY OF THE INVENTION

The invention features aromatherapy devices. In some aspects, an aromatherapy device comprises an upper portion having an open bottom, side walls comprising at least one opening, and at least one structure capable of breaking a breakable carrier, a lower portion having an open top and side walls comprising at least one opening and defining a chamber for holding a breakable carrier, and at least one fiber member in the lower portion capable of absorbing a liquid. The lower portion has a diameter smaller than the diameter of the upper portion and is configured to fit inside of the upper portion. In some aspects, an aromatherapy device comprises an upper portion comprising at least one opening that passes through the upper portion, a lower portion comprising at least one chamber for holding a breakable carrier and at least one structure capable of breaking the breakable carrier, and at least one fiber member in the lower portion capable of absorbing a liquid.

The aromatherapy device may further comprise a first ridge and a second ridge on the upper portion, and a third ridge and a fourth ridge on the lower portion. The first ridge engages the third ridge, and the second ridge engages the fourth ridge. The ridge engagement allows a user to rotate or slide the upper and lower portions of the device about each other.

The aromatherapy device may further comprise at least one breakable carrier that holds an aromatic liquid, which may be a fragrance, an aroma, or an essential oil.

The fragrance, aroma, or essential oil may include a scent of cherry, berry, clove, apple, pear, banana, orange, grapefruit, lemon, lime, peach, grape, lavender, lemongrass, coconut, mint, rosemary, menthol, tea tree, cedarwood, eucalyptus, litsea, mentha, cocoa, or vanilla, or a combination thereof. When the carrier is broken, its contents may diffuse into the fiber member, which may comprise cotton, alginate, rayon, or a combination thereof. The aromatherapy device may further comprise a heat source to heat the aromatic liquid. Heat may thus be used to facilitate release of the aroma.

The invention also features articles of clothing comprising an aromatherapy device. The article of clothing may be, for example, a surgical mask, a dust mask, a hospital gown, a shirt, or other article of clothing worn by a subject in need of aromatherapy.

The invention also features methods of aromatherapy. The methods may optionally comprise providing an aromatherapy device. In some aspects, the methods comprise placing a breakable carrier comprising an aromatic liquid into the chamber of the lower portion of an aromatherapy device comprising an upper portion having an open bottom, side walls comprising at least one opening, and at least one structure capable of breaking a breakable carrier, a lower portion having an open top and side walls comprising at least one opening and defining a chamber for holding the breakable carrier, and at least one fiber member in the lower portion capable of absorbing a liquid. In some aspects, the methods comprise placing a breakable carrier comprising an aromatic liquid into the chamber of the lower portion of an aromatherapy device comprising an upper portion comprising at least one opening that passes through the upper portion, a lower portion comprising at least one chamber for holding the breakable carrier and at least one structure capable of breaking the breakable carrier, and at least one fiber member in the lower portion capable of absorbing a liquid.

Once the breakable carrier comprising an aromatic liquid is in the chamber of the device, the upper and lower portions of the device are brought in proximity. Once the upper and lower portions of the device are in proximity, sufficient pressure is applied to each of the upper and lower portions to compress them together in order to break the carrier. After the carrier is broken and its liquid contents released, the openings of each of the upper and lower portions are aligned to allow the desired amount of aroma to flow out from the chamber of the aromatherapy device, for example, by rotating or sliding the upper or lower portion of the device back and forth until the opening is opened to a desired level.

The breakable carrier holds an aromatic liquid, which may be a fragrance, an aroma, or an essential oil. The fragrance, aroma, or essential oil may include a scent of cherry, berry, clove, apple, pear, banana, orange, grapefruit, lemon, lime, peach, grape, lavender, lemongrass, coconut, mint, rosemary, menthol, tea tree, cedarwood, eucalyptus, litsea, mentha, cocoa, or vanilla, or a combination thereof. When the carrier is broken, its contents may diffuse into the fiber member, which may comprise cotton, alginate, rayon, or a combination thereof. A heating step may be used to heat the aromatic liquid and facilitate release of the aroma.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

Various terms relating to aspects of the present invention are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

Figure 2:
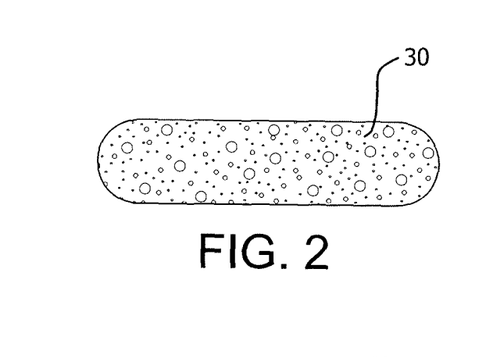
FIG. 2 shows an example of an absorbent fiber member.
Figure 3:
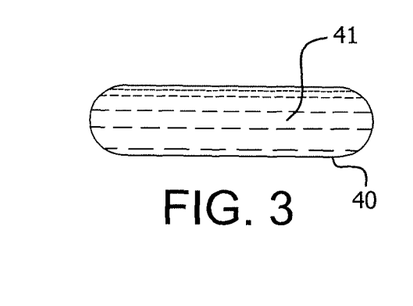
FIG. 3 shows an example of a breakable carrier comprising an aromatic liquid.

The invention provides aromatherapy devices and methods of releasing an aroma from an aroma therapy device, which provide a physiological, psychological, and/or emotional effect on a subject. In one embodiment shown in FIG. 1, an aromatherapy device 1 may comprise an upper portion 10 and a lower portion 20. The device 1 preferably also comprises a fiber member 30 (FIG. 2), and may house a breakable carrier 40 (FIG. 3). The device 1 may be of any size, and may be sized and shaped to fit into a holder into which the device 1 may be inserted, which may be present, for example, on an article of clothing. The components of the device 1 can be fabricated from any suitable material or combination of materials. Materials include plastic, polymers, glass, rubber, metal, and composites, preferably medical or surgical grade. In some preferred aspects, the upper portion 10 and the lower portion 20 of the device 1 comprise a rigid material, including a plastic or a polymer material that is rigid. In some preferred aspects, the upper portion 10 and lower portion 20 of the device 1 comprise a soft, flexible material, including, for example, a thin plastic or polymer material. The device 1 may be a single use device, or may be re-usable.

Figure 1:
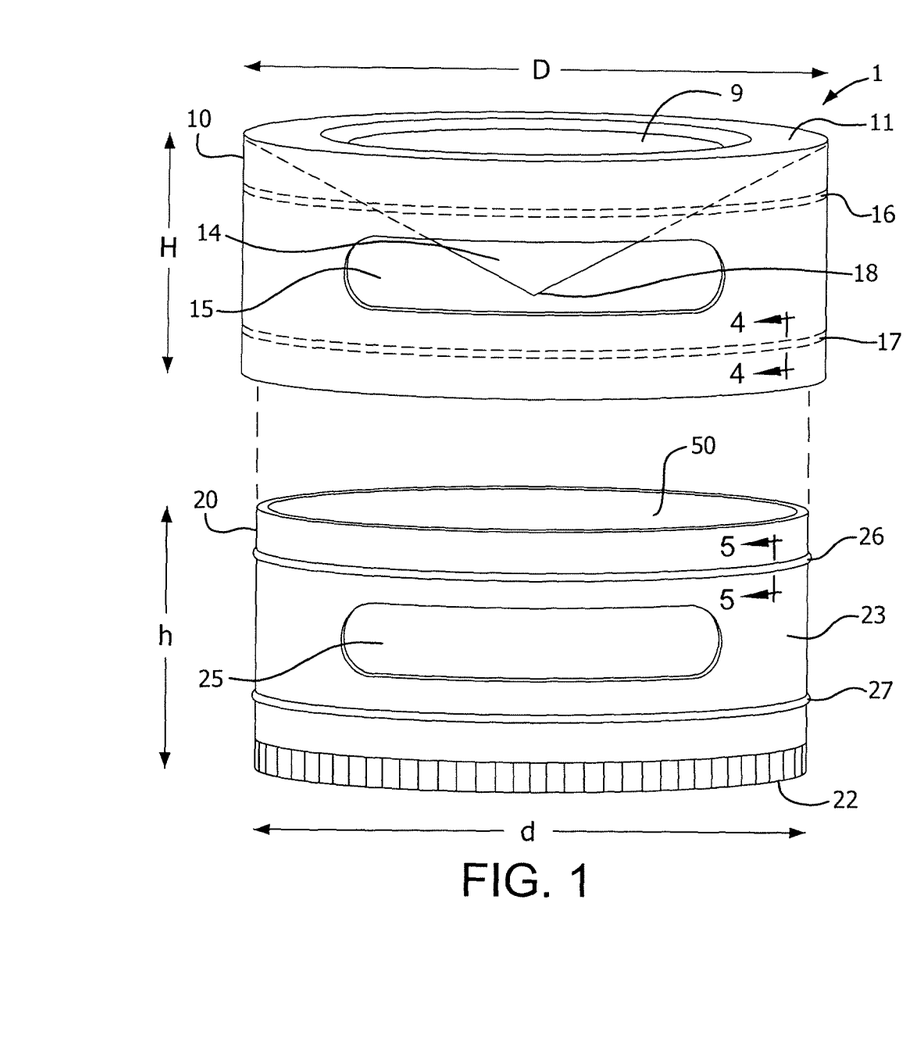
FIG. 1 shows an exploded side view of one embodiment of the aromatherapy device of the invention.
Figure 4:
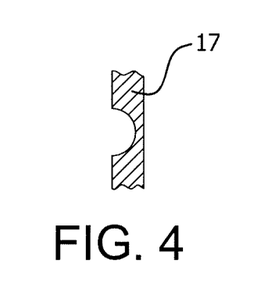
FIG. 4 shows an example of a concave ridge.
Figure 7:
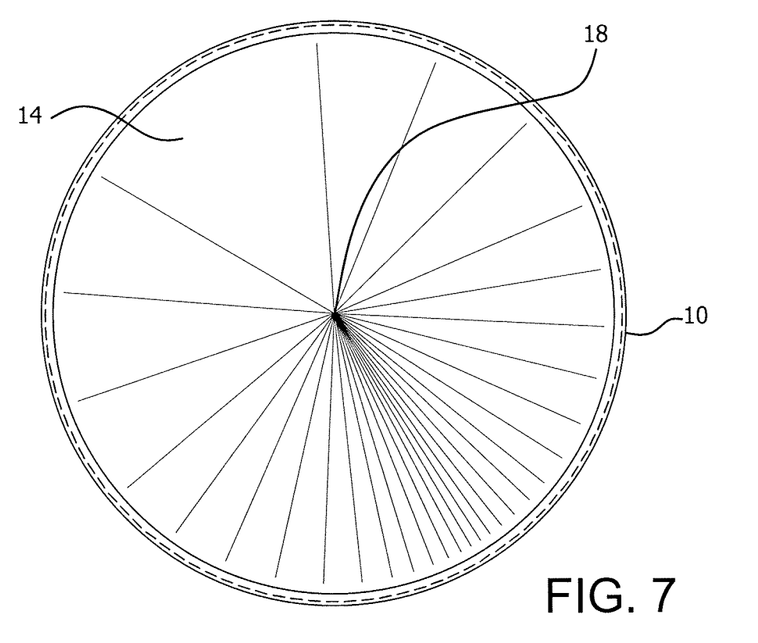
FIG. 7 shows a view of the tip of the upper portion of an aromatherapy device.

The upper portion 10 of the device 1 may comprise a top 11, a bottom 12 that is preferably open, and one or more side walls 13 that may have a substantially round shape, a substantially ovular shape, a substantially elliptical shape, or may have a substantially rectangular or substantially triangular shape. As shown in FIG. 1 and FIG. 7, the top 11 may comprise a conical or concave shape having a tip 14 at a center portion 9 of the top 11. The tip 14 preferably comprises one or more points 18. The tip 14 may be rounded or blunted, but in such aspects, should comprise a shape, projection, or structure sufficient to puncture a carrier 40 when the carrier 40 is inserted into the device 1 and the user of the device 1 compresses the upper portion 10 and lower portion 20 together. The upper portion 10 may comprise a first ridge 16 and may also comprise a second ridge 17 on the interior of the one or more side walls 13. The first ridge 16 and second ridge 17 may comprise a concave shape (e.g., FIG. 4).

The upper portion 10 may comprise at least one opening 15 (e.g., vent) on its one or more side walls 13. In addition to, or instead of the opening 15 on the one or more side walls 13, the upper portion 10 may comprise at least one opening 15 on the top 11, which openings 15 may be through the tip 14 (not shown). In some aspects, the upper portion 10 comprises two, three, four, five, six, seven, eight, nine, ten, or more openings 15. The upper portion 10 can have any number of openings 15 sufficient to release aroma from the device 1 during use.

Figure 5:
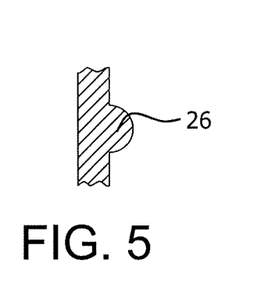
FIG. 5 shows an example of a convex ridge.

The lower portion 20 of the device 1 may comprise a top 21 that is preferably open, a bottom 22, and one or more side walls 23 that may have a substantially round shape, a substantially ovular shape, a substantially elliptical shape, or may have a substantially rectangular shape or substantially triangular shape. Preferably, the shape of the side walls 23 of the lower portion 20 has the same shape as the side walls 13 of the upper portion 10 such that the lower portion 20 may fit within the upper portion 10. Thus, it is preferred that the side walls 13 of the upper portion 10, when round, are configured with a diameter D that is slightly larger than the diameter d of the side walls 23 of the lower portion 20. The lower portion 20 may comprise a third ridge 26 and may also comprise a fourth ridge 27 on the exterior of the one or more side walls 23. The third ridge 26 and fourth ridge 27 may comprise a convex shape (e.g., FIG. 5). When the upper portion 10 and lower portion 20 of the device 1 are placed together (for example, the lower portion 20 may be configured to friction fit into interior of the upper portion 10 through the open bottom 12 of the upper portion 10), the first ridge 16 may interlock with the third ridge 26 and the second ridge 17 may interlock with the fourth ridge 27. The third ridge 26 and the fourth ridge 27 may comprise an O-ring or seal. The convex shape of the third ridge 26 and fourth ridge 27 preferably fits within the concave shape of the first ridge 16 and second ridge 17.

Figure 6:
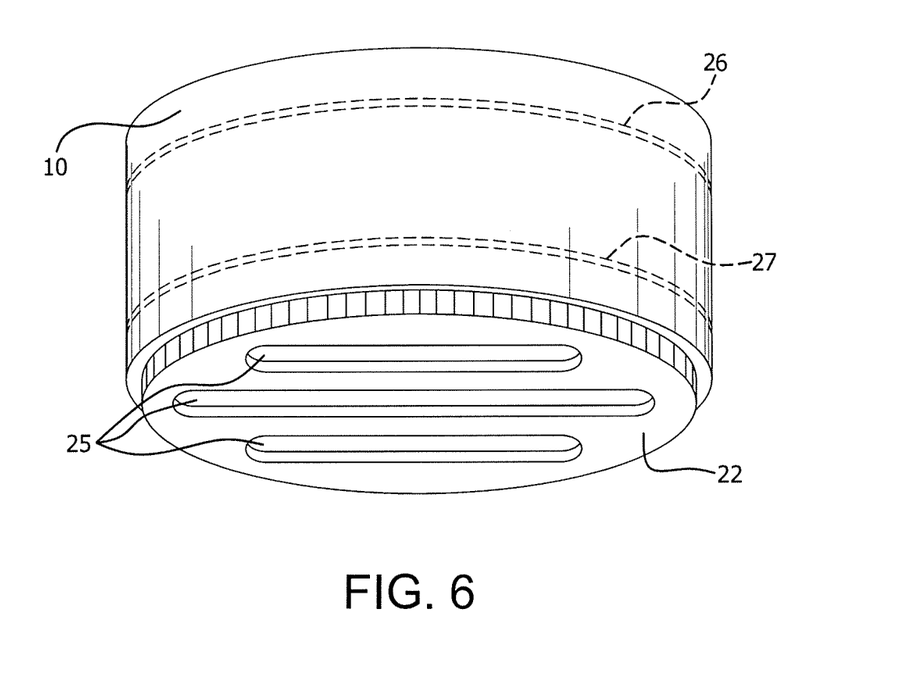
FIG. 6 shows an embodiment of an aromatherapy device having aroma-releasing vents on the bottom face.

The lower portion 20 may comprise at least one opening 25 (e.g., vent) on its one or more side walls 23. In addition to, or instead of the opening 25 on the one or more side walls 23, the lower portion 20 may comprise at least one opening 25 on the bottom 22, for example, as shown in FIG. 6. In some aspects, the lower portion 20 comprises two, three, four, five, six, seven, eight, nine, ten, or more openings 25. The lower portion 20 can have any number of openings 25 sufficient to release aroma from the device 1 during use.

In some preferred aspects, the openings 25 on the lower portion 20 and the openings 15 on the upper portion 10 align when the upper portion 10 and lower portion 20 are together in the device 1. The openings 25 on the lower portion 20 and the openings 15 on the upper portion 10 may, but need not, have an identical or substantially similar shape and size. In some aspects, the openings 25 of the lower portion 20 and/or the openings 15 of the upper portion 10 comprise a substantially round, ovular, elliptical, or rectangular shape. The openings 25 and 15 may be elongate.

The diameter D of the upper portion 10 may be about 20 mm to about 60 mm. The diameter D of the upper portion 10 may be about 25 mm to about 55 mm, about 25 mm to about 57 mm, about 25 mm to about 60 mm, about 27 mm to about 55 mm, about 30 mm to about 50 mm, about 30 mm to about 60 mm, about 35 mm to about 55 mm, about 35 mm to about 60 mm, about 40 mm to about 50 mm, about 40 mm to about 55 mm, about 40 mm to about 57 mm, about 40 mm to about 60 mm, about 45 mm to about 50 mm, about 50 mm to about 55 mm, about 50 mm to about 60 mm, or about 55 mm to about 60 mm. The diameter D may be about 20 mm, about 22 mm, about 25 mm, about 27 mm, about 30 mm, about 32 mm, about 35 mm, about 40 mm, about 50 mm, about 55 mm, or about 60 mm.

The diameter d of the lower portion 20 may be about 20 mm to about 60 mm. The diameter d of the lower portion 20 may be about 25 mm to about 55 mm, about 25 mm to about 57 mm, about 25 mm to about 60 mm, about 27 mm to about 55 mm, about 30 mm to about 50 mm, about 30 mm to about 60 mm, about 35 mm to about 55 mm, about 35 mm to about 60 mm, about 40 mm to about 50 mm, about 40 mm to about 55 mm, about 40 mm to about 57 mm, about 40 mm to about 60 mm, about 45 mm to about 50 mm, about 50 mm to about 55 mm, about 50 mm to about 60 mm, or about 55 mm to about 60 mm. The diameter d may be about 20 mm, about 22 mm, about 25 mm, about 27 mm, about 30 mm, about 32 mm, about 35 mm, about 40 mm, about 50 mm, about 55 mm, or about 60 mm. The diameter d is preferably slightly smaller than the diameter D for a given device 1. The difference in diameter D and diameter d is preferably sufficient that the lower portion 20 may fit snugly inside of the upper portion 10, and allow for the first 16, second 17, third 26, and fourth ridges 27 to engage and hold the upper portion 10 and lower portion 20 together and form the full device 1.

The height H of the upper portion 10 may be about 1 mm to about 30 mm. The height H may be about 1 mm to about 5 mm, about 1 mm to about 10 mm, about 5 mm to about 10 mm, about 5 mm to about 40 mm, about 10 mm to about 20 mm, about 10 mm to about 25 mm, about 10 mm to about 30 mm, about 15 mm to about 30 mm, about 20 mm to about 25 mm, about 20 mm to about 27 mm, about 20 mm to about 30 mm, or about 25 mm to about 30 mm. The height H may be about 5 mm, about 7 mm, about 9 mm, about 11 mm, about 13 mm, about 15 mm, about 17 mm, about 19 mm, about 21 mm, about 23 mm, about 25 mm, about 27 mm, or about 30 mm.

The height h of the lower portion 20 may be about 1 mm to about 30 mm. The height h may be about 1 mm to about 5 mm, about 1 mm to about 10 mm, about 5 mm to about 10 mm, about 5 mm to about 40 mm, about 10 mm to about 20 mm, about 10 mm to about 25 mm, about 10 mm to about 30 mm, about 15 mm to about 30 mm, about 20 mm to about 25 mm, about 20 mm to about 27 mm, about 20 mm to about 30 mm, or about 25 mm to about 30 mm. The height h may be about 5 mm, about 7 mm, about 9 mm, about 11 mm, about 13 mm, about 15 mm, about 17 mm, about 19 mm, about 21 mm, about 23 mm, about 25 mm, about 27 mm, or about 30 mm. The height h is preferably slightly smaller than the height h for a given device 1, to allow the lower portion 20 to fit substantially flush within the upper portion 10 with little or no amount of the bottom 22 extending out beyond the lower edge of the upper portion side walls 13.

When the upper portion 10 and lower portion 20 are placed together to form the device 1, the device 1 preferably assumes the diameter D of the upper portion 10 and the height H of the upper portion. This is because the lower portion 20 is preferably configured to fit within the upper portion 20. The configuration of the upper portion 10 and lower portion 20 of the device 1 may, however, be reversed such that the upper portion 10 is configured to fit within the lower portion 20, in which case the device 1 may assume the diameter d of the lower portion 20.

Figure 8:
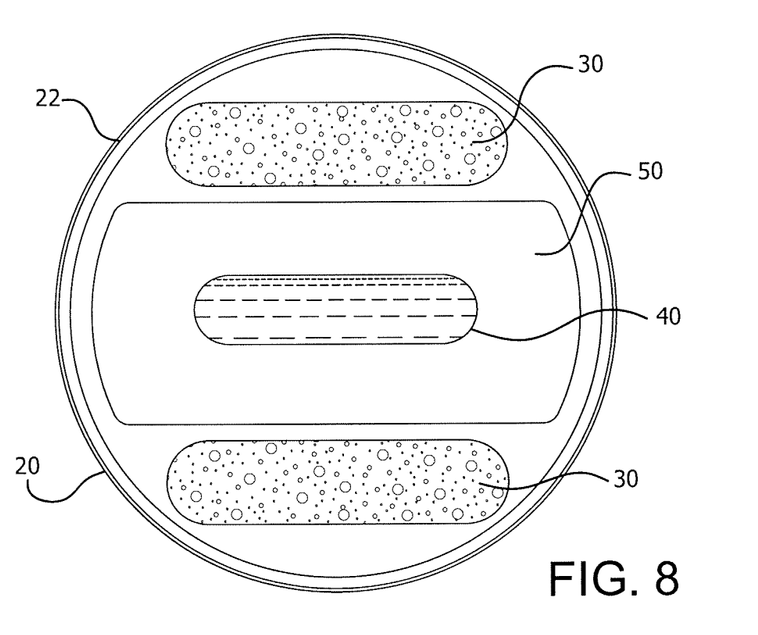
FIG. 8 shows a view of the interior of the lower portion of the aromatherapy device, including the placement of a breakable carrier and absorbent fiber members.

The side walls 13 and 23 of the device 1 define a chamber 50 into which a carrier 40 of a scented material such as a liquid 41 may be placed (FIG. 1, FIG. 8). The openings 15 and 25 of the device 1 provide access to the chamber 50 from the outside of the device 1, and also allow the scent from the material to be released from the device 1.

The carrier 40 preferably stores the scented material, such as a liquid 41 to be dispersed (FIG. 3), until the user of the device 1 engages the device 1 to release the scent. The carrier 40 may be made of any material that is frangible or breakable upon the application of pressure, including but not limited to a polymer, foil, glass, ceramic, or plastic. The carrier 40 may be filled, for example, with scented materials that include essential oils, fragrances, aromas, or compositions comprising one or more fragrances, aromas, or essential oils. The carrier 40 preferably has dimensions suitable to allow the carrier 40 to fit in the chamber of the device 1.

The oils may be natural or synthetic oils, or may comprise a mixture of both. Natural oils include plant and animal oils. For example, the carrier 40 may be filled with organic, therapeutic grade essential oils. The liquid 41 may comprise volatile aromatic or chemical liquids. The liquid 41 may comprise any desirable fragrance, aroma, essential oil, or composition comprising a fragrance, aroma, or essential oil. Non-limiting examples of scents include cherry, berry, clove, apple, pear, banana, orange, grapefruit, lemon, lime, peach, grape, lavender, lemongrass, coconut, mint, rosemary, menthol, tea tree, cedarwood, eucalyptus, litsea, mentha, cocoa, vanilla, and any other scent a consumer prefers, as well as combinations thereof. The scents may be those that are known to have an anti-nausea or aromatherapeutic effect. The liquid 41 may also comprise a medicine. The liquid 41 may also contain other chemicals to enhance preservation, activation, or stabilization. The liquid 41 may also contain an antimicrobial agent to prevent microbe-contamination of the oil.

Preferably, the device 1 comprises a single carrier 40. However, the device 1 may comprise more than one carrier 40, for example, if a user desires to use multiple scents, or combine scents. A single carrier 40 may contain more than one different scented liquid 41, including more than one oil or fragrance. The size and shape of the carrier 40 may vary, for example, to accommodate different volumes of liquid 41 or different sized devices 1.

Figure 9:
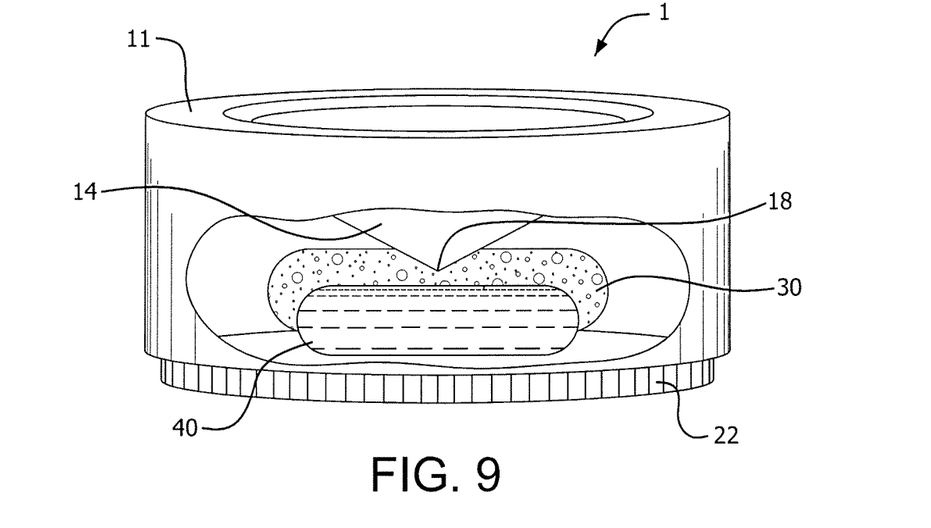
FIG. 9 shows the upper and lower portions of an aromatherapy device in proximity such that the pointed tip of the upper portion is ready to compromise the breakable carrier.
Figure 10:
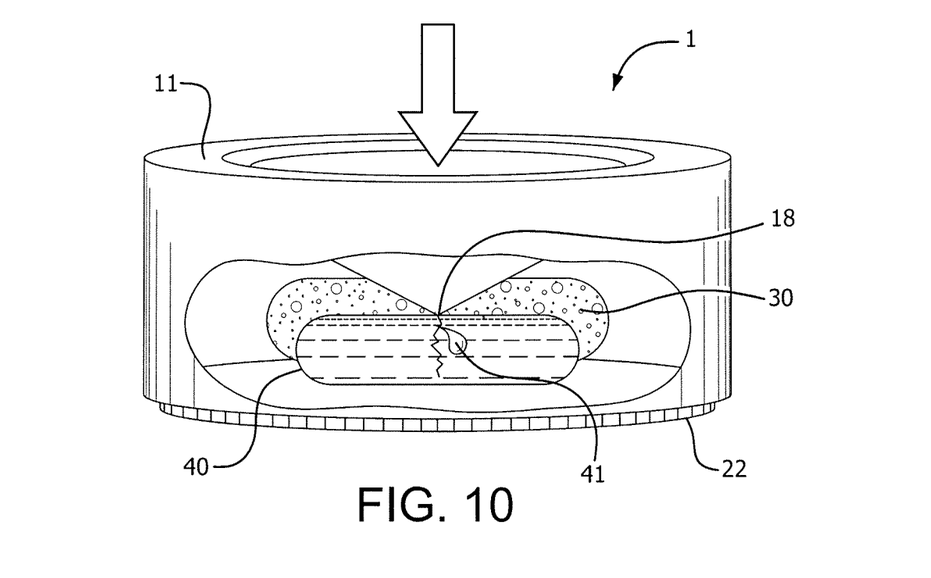
FIG. 10 shows the upper and lower portions of an aromatherapy device in closer proximity such that the lower portion is further inside of the upper portion, and the pointed tip has compromised the breakable carrier and the aromatic liquid is flowing out from the carrier.
Figure 11:
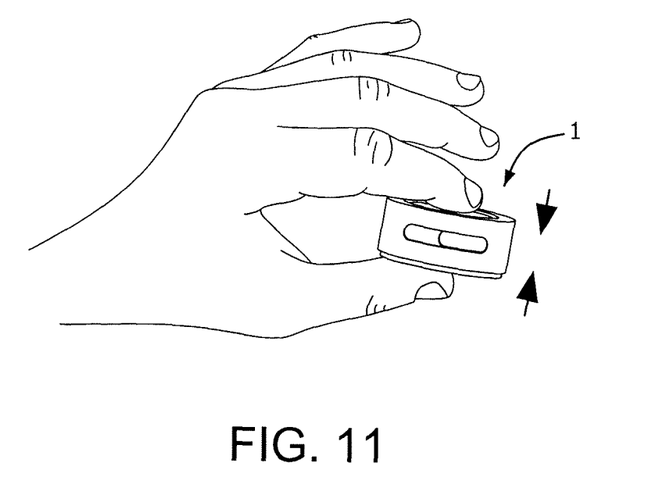
FIG. 11 shows an aromatherapy device being activated by squeezing the upper and lower portions together between a user's fingers.

To release the aroma from the device 1, a breakable carrier 40 containing a desired scented material such as the liquid 41 is placed into the chamber 50 of the device 1 (FIG. 8, FIG. 9). For example, the chamber 50 may be accessed through an opening in the top 21 of the lower portion 20. The lower portion 20 containing the carrier 40 is then placed inside of the upper portion 10 (for example, the lower portion 20 may be inserted into the open bottom 12 of the upper portion 10), to assemble the device 1 (FIG. 9). A user may then apply pressure to the top 11 of the upper portion 10 and the bottom 22 of the lower portion 20 (FIG. 10). For example, as shown in FIG. 11, the device 1 may be pressurized between the fingers and thumb of a human hand. However, pressure may be applied to the upper portion 10 and the lower portion 20 of the device 1 according to any suitable method, including squeezing the device 1 between hands, feet, solid surfaces, pliers, and any other object that is capable of applying pressure.

When pressure is applied to the device 1, the upper portion 10 slides firmly over the lower portion 20 (FIG. 9 and FIG. 10). As the upper portion 10 slides downward, the tip 14, including any point 18 or other structure or projection initially contacts the outer surface of the carrier 40, and punctures or otherwise breaks the outer surface of carrier 40 (FIG. 10). As the carrier 40 breaks, the liquid 41 is released from the carrier 40, and diffuses into to the fiber member 30, which then absorbs the liquid 41. The upper portion 10 is capable of sliding downward over the lower portion 20 until the second ridge 17 interlocks with the fourth ridge 27 and the first ridge 16 interlocks with the third ridge 26 (FIG. 1). The first 16, second 17, third 26, and fourth 27 ridges may snap-fit or friction fit, or comprise a track and rib configuration to fit together (e.g., the convex ridge may fit together inside of the concave ridge).

Once the liquid 41 is taken up by the fiber member 30, the volatile vapor and aroma from the liquid 41 is released from the device 1 outward through the openings 15 and 25, which overlap each other when the upper portion 10 and lower portion 20 of the device 1 are compressed together (FIG. 1 and FIG. 12) and the openings 15 and 25 are aligned.

The fiber member 30 is capable of absorbing the liquid 41 and thereby allowing release of an aroma from the liquid 41. Depending on the scent chosen, one or multiple effects can be obtained from smelling the different scents. There is at least one fiber member 30, but there may be more than one (FIG. 8). In some aspects, there are two fiber members 30. The size and shape of the fiber member 30 may vary, but preferably, the fiber member 30 is elongated to better hold and diffuse aromas from the absorbed liquid 41. The fiber member 30 may be a made of a fiber material capable of absorbing and holding liquid, which may include cotton, cloth, alginate, rayon, cotton mixed with other fibers, or any other suitable absorbent material. As shown in FIG. 8, the fiber members 30 may be positioned within the lower portion 20 of the device. In some aspects, the fiber members 30 are located at one or more sides of the carrier 40.

Figure 12:
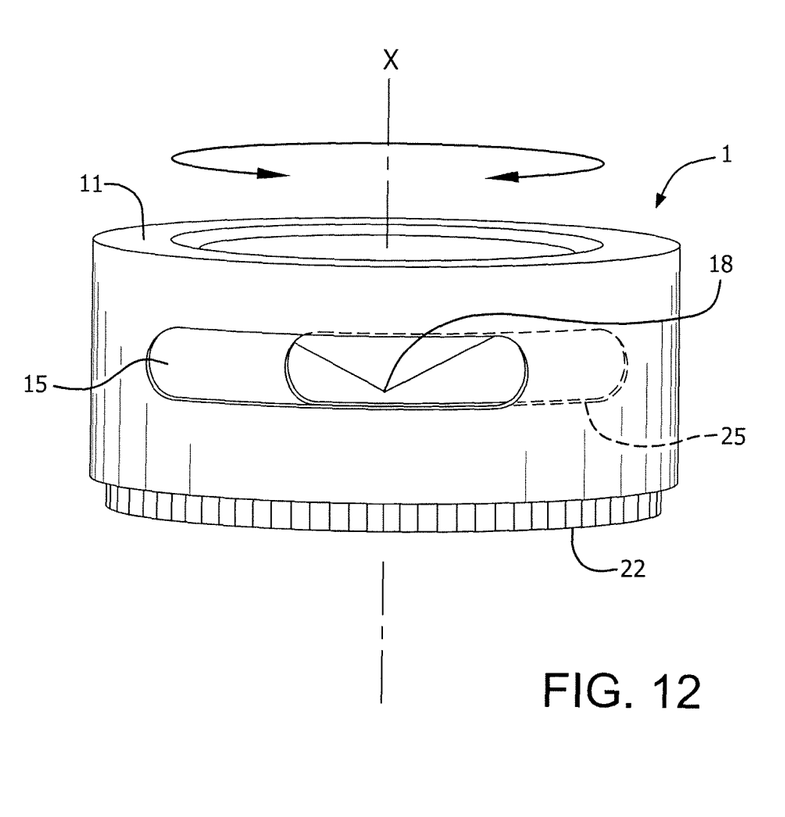
FIG. 12 shows how an aromatherapy device can be rotated to open or close the opening and control the amount of scent released from the device.

In some aspects, to control the amount of aroma released, the upper portion 10 or lower portion 20 may be rotated clockwise or counterclockwise around an axis X and about the lower portion 20 or upper portion 10, respectively (FIG. 12). As the portions 10 and 20 are rotated about the axis X, the openings 15 and 25 may be partially obstructed by the side walls 13 and 23 such that less of the aroma is released. The openings 15 and 25 may be fully opened for maximal release of the aroma (no obstruction from the side walls 13 and 23), or may be partially opened/closed for limiting the release of the aroma (partial obstruction from the side walls 13 and 23, e.g., FIG. 12), or may be fully closed to minimize or stop the release of the aroma (the openings 15 and 25 will no longer overlap, and the side walls 13 and 23 will fully obstruct the openings). When the openings 15 and 25 do not overlap at all, they are fully closed. The degree to which the openings 15 and 25 overlap is controlled by the user, who may rotate the upper portion 10 and lower portion 20 at will.

Figure 13:
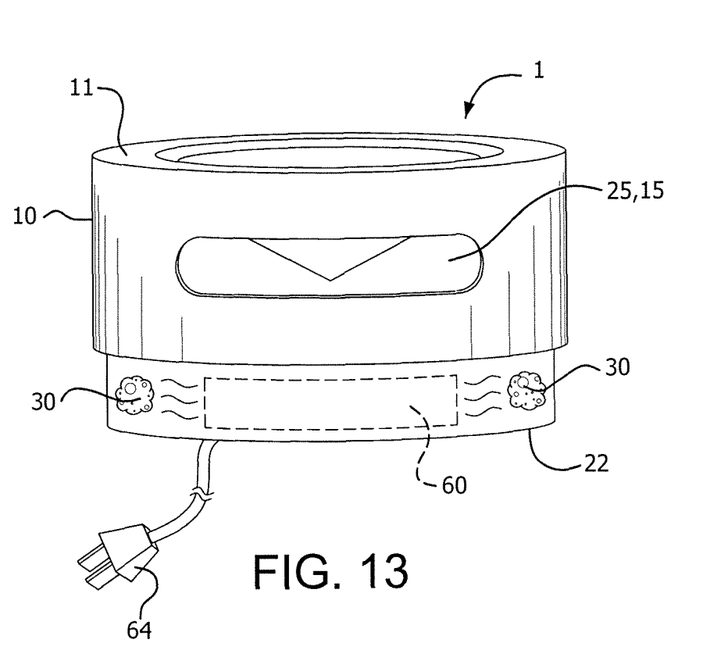
FIG. 13 shows a side view of an embodiment of the aromatherapy device with a heat source.
Figure 14:
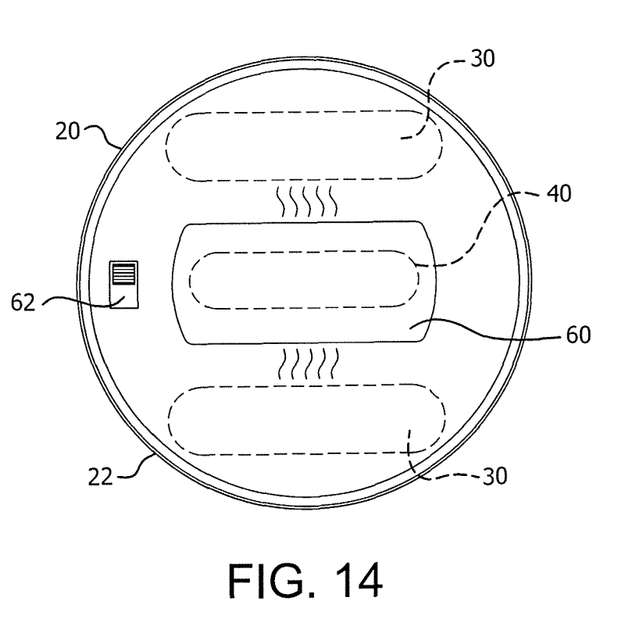
FIG. 14 shows a bottom perspective of an aromatherapy device with the heat source.

In some aspects, the device 1 may include a heat source 60 to heat the liquid 41 absorbed by the fiber member 30 (FIG. 13). The heat source 60 may also be used to maintain the liquid 41 at a desired temperature before and after release. The heat source 60 may be located in bottom 22 of the lower portion 20 (FIG. 13, FIG. 14), or may be separately attachable to the device 1 in another location. The heat source 60 may be powered by an external power source (including an AC or DC circuit, or external battery), or may be powered by a battery in the device 1 (not shown). The heat source may be operably connected to an on and off switch 62 and/or plug 64 for an electrical outlet, cigarette lighter in an automobile, or some other suitable power supply.

Figure 18:
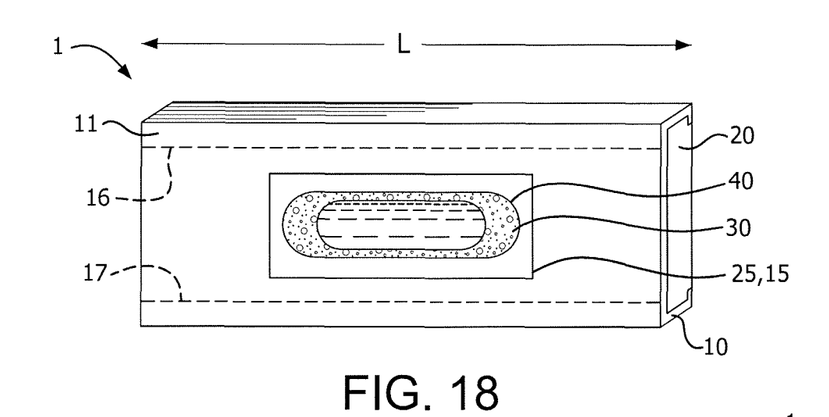
FIG. 18 shows a thin, flexible embodiment of an aromatherapy device that may be used with a surgical mask.
Figure 19:
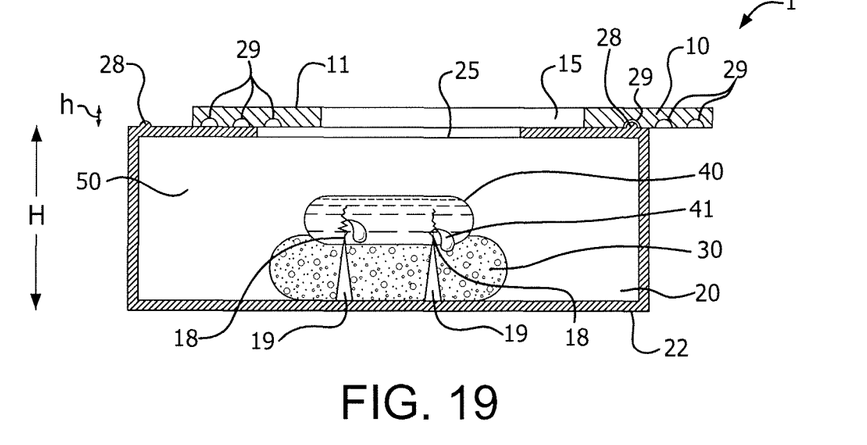
FIG. 19 shows a side perspective of a thin, flexible embodiment of an aromatherapy device with the upper portion partially extended by sliding outward.
Figure 20:
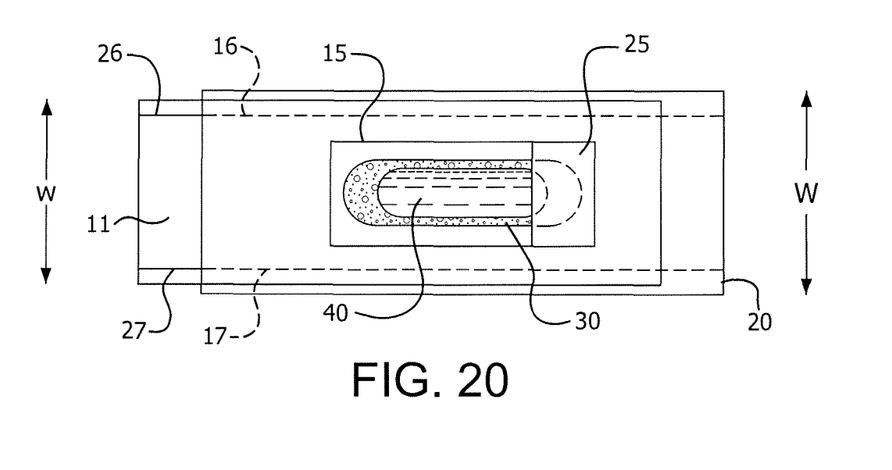
FIG. 20 shows a top perspective of a thin, flexible embodiment of an aromatherapy device with the upper portion partially extended.

In some embodiments, the device 1 has a thin, and preferably flexible, profile, and is suitable for insertion into a pocket on a mask with minimal or no irritation or discomfort to the wearer of the mask caused by the presence of the device 1 in the mask. In some aspects, the upper portion 10 of the device 1 comprises a top 11 and a bottom 12, and optionally comprises one or more side walls 13. In this embodiment, the upper portion has a substantially square or rectangular shape, and is configured to be slidably positioned on top of the lower portion 20 in an assembled device 1. See FIG. 18-20. The upper portion 10 comprises at least one opening 15 present on the top 11. In some aspects, the upper portion 10 comprises two, three, four, five, six, seven, eight, nine, ten, or more openings 15. The upper portion 10 can have any number of openings 15 sufficient to release aroma from the device 1 during use. FIGS. 18-20 show one configuration with one opening for illustration purposes.

In this thin profile embodiment, the lower portion 20 of the device 1 comprises a top 21 and a bottom 22, and has a substantially square or rectangular shape, and is configured to be slidably positioned under the upper portion 10 in an assembled device 1. The lower portion 20 comprises at least one chamber 50 into which at least one carrier 40 of a scented material may be placed. The at least one chamber 50 may comprise one or more structures 19 having a tip 18 capable of puncturing the carrier 40 when the carrier 40 is inserted into the chamber 50. The at least one chamber 50 may also comprise one or more fiber members 30 for absorbing materials such as a liquid 41 released from the carrier 40. The at least one chamber 50 preferably is open at the top which can align with the opening 15 of the upper portion. The device 1 may comprise two, three, four, five, or more chambers 50. Each chamber may comprise one or more structures 19 having a tip 18 for puncturing a carrier 40, and one or more fiber members 30 for absorbing a liquid, and each chamber may be used to contain a separate carrier 40. Thus, multiple carriers 40 with different aromas may be used in accordance with such aspects.

The upper portion 10 may comprise a first ridge 16 and a second ridge 17 on the bottom surface 12. The lower portion 20 may comprise a third ridge 26 and a fourth ridge 27 on its top surface 21. The first ridge 16 and second ridge 17 may comprise a convex shape, and the third ridge 26 and fourth ridge 27 may comprise a concave shape. When the upper portion 10 is placed over top of the lower portion 20, the first ridge 16 may mate with the third ridge 26, and the second ridge 17 may mate with the fourth ridge 27, for example, with a snap fit, or a slidable friction fit. Thus, the ridges 16, 17, 26, and 27 may facilitate alignment of the upper 10 and lower portions 20, may hold the upper 10 and lower portions 20 together, and may function as a track to allow the upper portion 10 to slide back and forth in a horizontal plane over the lower portion 20.

Optionally, the top surface 21 of the lower portion 20 may comprise a plurality of tabs 28 that are composed of a flexible plastic or polymeric material, that project upward when not compressed down, for example, by being compressed when the upper potion 10 is placed on top of the lower portion 20. Optionally, the bottom surface 12 of the upper portion 10 may comprise a plurality of slots 29 that align with the plurality of tabs 28, into which the tabs 28 may extend when the tabs 28 are not compressed down. The tabs 28 and slots 29, if present, may facilitate alignment of the upper 10 and lower portions 20, may hold the upper 10 and lower portions 20 together, and may function as to prevent the upper portion 10 from sliding off of the lower portion 20.

The width W of the upper portion 10 may be about 15 mm to about 40 mm. The width W may be about 20 mm to about 40 mm, about 20 mm to about 35 mm, about 25 mm to about 40 mm, about 25 mm to about 35 mm, about 30 mm to about 40 mm, or about 35 mm to about 40 mm. The width W may be about 15 mm, about 17 mm, about 19 mm, about 21 mm, about 23 mm, about 25 mm, about 27 mm, about 29 mm, about 31 mm, about 33 mm, about 35 mm, about 37 mm, or about 40 mm. The width w of the lower portion 20 may be about 15 mm to about 40 mm. The width w may be about 20 mm to about 40 mm, about 20 mm to about 35 mm, about 25 mm to about 40 mm, about 25 mm to about 35 mm, about 30 mm to about 40 mm, or about 35 mm to about 40 mm. The width w may be about 15 mm, about 17 mm, about 19 mm, about 21 mm, about 23 mm, about 25 mm, about 27 mm, about 29 mm, about 31 mm, about 33 mm, about 35 mm, about 37 mm, or about 40 mm. The width w is preferably slightly smaller than the width W for a given device 1.

The length L of the upper portion 10 may be about 25 mm to about 100 mm. The length L may be about 50 mm to about 90 mm, about 55 mm about 95 mm, about 60 mm to about 80 mm, about 60 mm to about 90 mm, about 75 mm to about 85 mm, about 80 mm to about 100 mm, about 80 mm to about 90 mm, about 85 mm to about 95 mm, or about 90 mm to about 100 mm. The length L may be about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, or about 100 mm. The length l of the lower portion 20 may be about 25 mm to about 100 mm. The length l may be about 50 mm to about 90 mm, about 55 mm about 95 mm, about 60 mm to about 80 mm, about 60 mm to about 90 mm, about 75 mm to about 85 mm, about 80 mm to about 100 mm, about 80 mm to about 90 mm, about 85 mm to about 95 mm, or about 90 mm to about 100 mm. The length l may be about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, or about 100 mm. The length l and length L may be substantially the same.

In embodiments where the device has a very thin and flexible profile, the height H of the upper portion 10 may be about 0.1 mm to about 3 mm. The height H may be about 0.5 mm to about 1.5 mm, about 0.5 mm to about 1.3 mm, about 0.5 mm to about 1.1 mm, about 0.5 mm to about 2 mm, about 1 mm to about 1.8 mm, about 1 mm to about 2 mm, about 0.8 mm to about 1.8 mm, or about 0.8 mm to about 1.5 mm. The height H may be about 0.1 mm, about 0.3 mm, about 0.5 mm, about 0.7 mm, about 0.9 mm, about 1.1 mm, about 1.3 mm, about 1.5 mm, about 1.7 mm, about 1.9 mm, about 2.1 mm, about 2.3 mm, about 2.5 mm, about 2.7 mm, or about 3 mm. The height h of the lower portion 20 may be about 0.5 mm to about 10 mm. The height h may be about 0.5 to about 5 mm, about 1 mm to about 8 mm, about 2 mm to about 6 mm, about 3 mm to about 9 mm, about 3 mm to about 10 mm, about 4 mm to about 6 mm, or about 5 mm to about 7 mm. The height h may be about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, or about 10 mm.

To release the aroma from the thin profile embodiment of the device 1, a carrier 40 containing a desired scented material such as the liquid 41 is placed into the chamber 50 of the device 1 (FIGS. 18-20). The upper portion 10 is then secured in place over the lower portion 20 containing the carrier 40 (for example, the upper portion 10 may be slid over top of the lower portion 20), to assemble the device 1. A user may then apply pressure to the top 11 of the upper portion 10 and the bottom 22 of the lower portion 20. For example, the device 1 may be pressurized between the fingers and thumb of a human hand, or according to any suitable method, including squeezing the device 1 between hands, feet, solid surfaces, pliers, and any other object that is capable of applying pressure. A user may simply apply pressure directly to the carrier 40 such that the tip 18 punctures the carrier 40.

When pressure is applied to the device 1 or directly to the carrier 40, the tip 18 initially contacts the outer surface of the carrier 40, and punctures or otherwise breaks the outer surface of carrier 40. As the carrier 40 breaks, the liquid 41 is released from the carrier 40, and diffuses into to the fiber member 30, which then absorbs the liquid 41. Once the liquid 41 is taken up by the fiber member 30, the aroma from the liquid 41 is released from the device 1 outward through the one or more openings 15, 25.

To control the amount of aroma released, the user may slide the upper portion 10 back and forth over the lower portion 20 (FIGS. 18-20). As the upper portion 10 slides over the lower portion 20, the one or more openings 15 may be partially obstructed such that less of the aroma is released. The one or more openings 15 may be fully opened for maximal release of the aroma (no obstruction), or may be partially opened/closed for less release of the aroma (partial obstruction, e.g., FIGS. 19 and 20), or may be fully closed to minimize or stop the release of the aroma. The degree to which the one or more openings are over the chamber 50 is controlled by the user, who may slide the upper portion 10 at will. The tabs 28 and slots 29 may help to keep the upper portion 10 from sliding off of the lower portion 20 as the user slides the upper portion 10.

Figure 15:
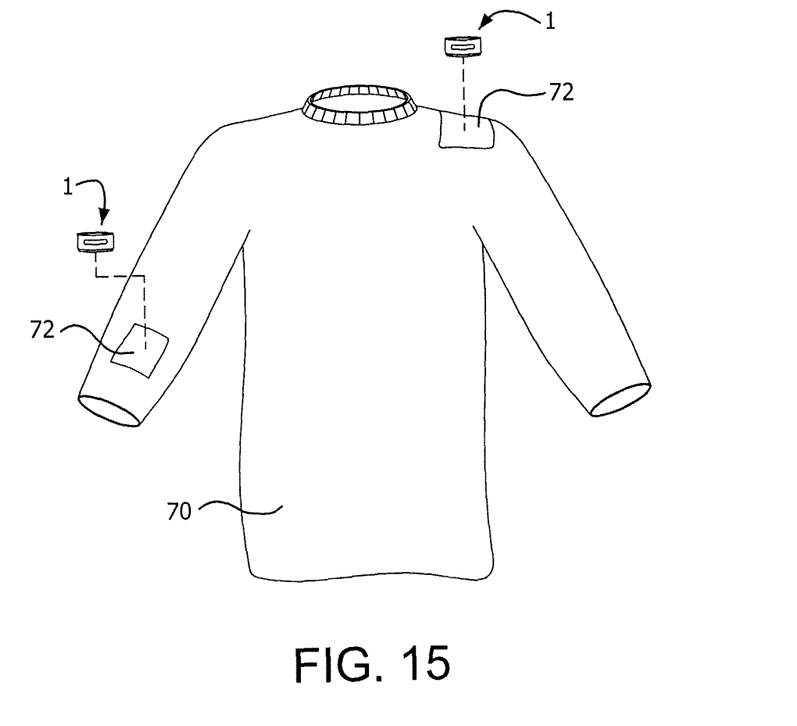
FIG. 15 shows a shirt with a pocket for an aromatherapy device; The pocket may be present on any suitable location on the shirt, examples of which include the shoulder area or the sleeve, as shown.
Figure 16:
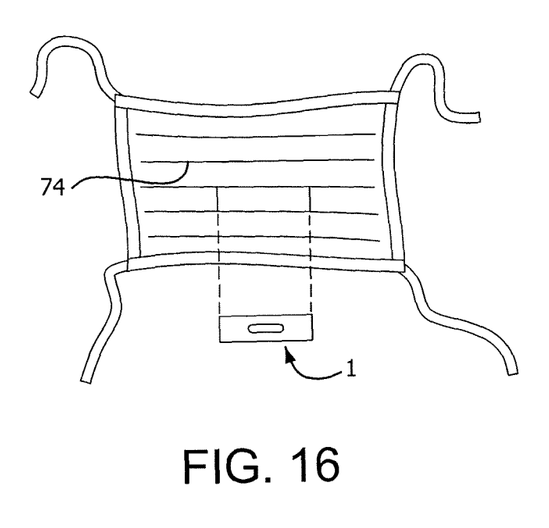
FIG. 16 shows a surgical mask compatible with an aromatherapy device.
Figure 17:
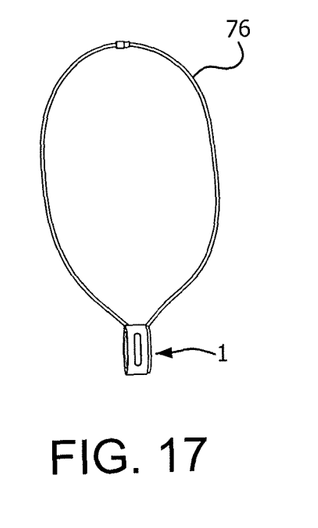
FIG. 17 shows an aromatherapy device as a pendant.

Any embodiment of the device 1 is preferably inserted into a suitable pocket 72 in an article of clothing 70 (FIG. 15). The article of clothing 70 may be, for example, a hospital gown, a shirt, a blouse, pajamas, a hat, a scarf, a mitten or glove, a pair of pants, a sock, a head band, a wrist band, jewelry, or other suitable article of clothing 70. The pocket 72 may be present on the shoulder or sleeve portion of a shirt or gown, or in a traditional shirt pocket. The device 1 may also be inserted into a suitable pocket 72 in a mask 74 such as a construction/dust mask or surgical mask (FIG. 16). In some aspects, the device 1 may be used as a pendant 76 placed around the neck of a user (FIG. 17). The device 1 may comprise an adhesive (not shown) on the top 11 or bottom 22 section that may allow a user to stick the device 1 to any article of clothing 70 at any location according to their preference.

In some aspects, the device 1 is provided as a kit, for example, with one or more breakable carriers 40 comprising an aromatic liquid 41. The kit may comprise instructions for using the device in a method for providing a desired aroma to a subject, such as for aromatherapy or for masking an unpleasant scent. A kit may further comprise fiber members 30, such that used fiber members 30 may be removed from the device 1 and replaced, ready to receive a new aromatic liquid 41.

The device 1 may be used to provide a desired aroma to a subject, for example, a subject in need of aromatherapy or a subject that desires to mask an unpleasant scent in the environment. Individuals may use the aromatherapy device 1 to smell various scents in almost any location. These locations can include but are not limited to places where anti-nausea scents may be helpful, or where unpleasant odors are present. In this latter case, the device 1 may be used to mask unpleasant odors while the user is present in the odor-containing location. Users of the device 1 including surgical or medical procedure/post-anesthesia recovery patients, chemotherapy patients, pregnant women suffering from morning sickness, persons who are susceptible to or are suffering from motion sickness, patients with a sinus infection or condition, surgeons in an operating room, day spa/salon customers, athletes, or any other individual in any situation who desires to smell a pleasant scent and/or engage in aromatherapy, for any desired purpose. For example, loaded with a pleasant aroma, the aromatherapy device 1 may be utilized in or on surgical masks to cover noxious odors in the operating room. The aromatherapy device 1 may also be used by chemotherapy patients to combat nausea induced by the chemotherapeutic agents. The bronchodilation effects induced by many scents can be used by athletes to overcome bronchoconstriction (tightening of the airways) from competition and exercise in order to improve performance and endurance. The relaxation effects of many scents can be used in individuals in stressful situation, such as students preparing for exams or employees at work, as well as many other situations. There are vast numbers of other scents that can elicit a plethora of different positive emotional and physiological responses as well.

Although the invention has been described in detail and with reference to specific embodiments, it will be apparent to one skilled in the art that various changes and modifications can be made without departing from the spirit and scope of the invention. The aromatherapy device 1 may also be used for other animals aside from human beings. Thus, the invention is capable of variation and modification within the scope of the appended claims.

The invention claimed is:

1. An aromatherapy device, comprising an upper portion having a top, an open bottom, side walls comprising an interior side, an exterior side, and at least one opening, a first groove and a second groove extending circumferentially around the interior side of the side walls of the upper portion, and at least one structure capable of breaking a breakable carrier;
   a lower portion having a bottom including at least one fiber member thereon capable of absorbing a liquid, an open top, and side walls comprising an interior side, an exterior side, and at least one opening therethrough, a first seal and a second seal extending circumferentially around the exterior side of the side walls of the lower portion, and said lower portion defining a chamber for holding the breakable carrier,
   wherein the lower portion has a diameter smaller than the diameter of the upper portion and is configured to fit inside of the upper portion, and wherein the first seal interlocks with the first groove and the second seal interlocks with the second groove to hold the upper portion and the lower portion together and allow full clockwise or counterclockwise rotation of the upper and lower portions about a rotation axis.

2. The aromatherapy device of claim 1, wherein the breakable carrier comprises an aromatic liquid.

3. The aromatherapy device of claim 2, wherein the aromatic liquid is a fragrance, aroma, or essential oil.

4. The aromatherapy device of claim 1, wherein the fiber member comprises cotton, alginate, rayon, or a combination thereof.

5. The aromatherapy device of claim 1, further comprising a heat source.

6. An article of clothing, comprising an article of clothing comprising the aromatherapy device of claim 1.

7. A kit, comprising the aromatherapy device of claim 1 and a breakable carrier comprising an aromatic liquid.

8. The kit of claim 7, wherein the aromatic liquid is a fragrance, aroma, or essential oil.

9. A method of aromatherapy comprising: placing a breakable carrier comprising an aromatic liquid into the chamber of the lower portion of the aromatherapy device of claim 1, placing the lower portion into the upper portion of the aromatherapy device of claim 1, applying pressure to the upper portion and the lower portion sufficient to break the carrier, and aligning the at least one opening of the upper portion and the at least one opening of the lower portion to allow vapors from the aromatic liquid to flow out from the chamber of the aromatherapy device.

10. The method of claim 9, further comprising rotating the upper portion or the lower portion of the aromatherapy device to control the amount of vapors from the aromatic liquid flowing out from the chamber.

11. The method of claim 9, further comprising warming the aromatic liquid with a heat source.

12. The method of claim 9, wherein the aromatic liquid is a fragrance, aroma, or essential oil.

13. The method of claim 9, wherein the subject is a chemotherapy patient.

14. The method of claim 9, further comprising placing the aroma therapy device in an article of clothing.

15. An aromatherapy device, comprising an upper portion having a top, an open bottom, side walls having an interior side and an exterior side without any openings therethrough, a first groove and a second groove extending circumferentially around the interior side of the side walls of the upper portion, and at least one structure capable of breaking a breakable carrier;
- a lower portion having a bottom comprising one or more openings, an open top and side walls having an interior side and an exterior side and without any openings therethrough, a first seal and a second seal extending circumferentially around the exterior side of the side walls of the lower portion, and at least one fiber member capable of absorbing a liquid, said lower portion defining a chamber for holding the breakable carrier,
- wherein the lower portion has a diameter smaller than the diameter of the upper portion and is configured to fit inside of the upper portion, and wherein the first seal interlocks with the first groove and the second seal interlocks with the second groove to hold the upper portion and the lower portion together and allow full clockwise or counterclockwise rotation of the upper and lower portions about a rotation axis.

16. The aromatherapy device of claim 15, wherein the breakable carrier comprises an aromatic liquid.

17. The aromatherapy device of claim 16, wherein the aromatic liquid is a fragrance, aroma, or essential oil.

18. The aromatherapy device of claim 15, wherein the at least one fiber member is on the bottom of the lower portion.

19. The aromatherapy device of claim 15, wherein the fiber member comprises cotton, alginate, rayon, or a combination thereof.

20. A kit, comprising the aromatherapy device of claim 15 and a breakable carrier comprising an aromatic liquid.

21. The kit of claim 20, wherein the aromatic liquid is a fragrance, aroma, or essential oil.

* * * * *